United States Patent [19]

Lewis

[11] 3,933,421

[45] Jan. 20, 1976

[54] POLYMER TREATMENT OF FIBROUS AND FILAMENTARY MATERIALS

[75] Inventor: David Malcolm Lewis, Otley, England

[73] Assignee: I.W.S. Nominee Company Limited, London, England

[22] Filed: Dec. 5, 1972

[21] Appl. No.: 312,357

[30] Foreign Application Priority Data
Dec. 9, 1971 United Kingdom............... 57313/71
Feb. 7, 1972 United Kingdom................. 5643/72

[52] U.S. Cl. ........................... 8/10; 8/1 Q; 8/10.1; 8/30; 8/120; 8/115.5; 8/128 A; 8/128 R; 8/DIG. 4; 428/420
[51] Int. Cl.²... D06P 1/86; D06Q 1/02; D06M 3/06
[58] Field of Search.......... 8/128 A, 120, 128 R, 30, 8/10, 1 Q, 10.1, 115.5, DIG. 4; 428/240

[56] References Cited
UNITED STATES PATENTS

| | | | |
|---|---|---|---|
| 2,400,377 | 5/1946 | Speakman | 8/128 R |
| 2,615,783 | 10/1952 | Haefle | 8/128 R |
| 3,005,713 | 10/1961 | Dersch | 96/114.8 |
| 3,693,633 | 9/1972 | Kalopissis | 8/127.51 |

FOREIGN PATENTS OR APPLICATIONS

| | | | |
|---|---|---|---|
| 1,002,325 | 8/1965 | United Kingdom | 8/1 Q |
| 1,013,829 | 12/1965 | United Kingdom | 8/1 Q |

*Primary Examiner*—Donald Levy
*Attorney, Agent, or Firm*—Dennis P. Clarke

[57] ABSTRACT

A process for the treatment of natural and/or synthetic fibrous and filamentary materials, including living human hair, which involves applying to the fibrous or filamentary materials a polymeric compound containing at least one poly (oxyalkylene) or polyamide chain and at least one thiosulphuric acid or thiosulphate group. Such compounds having more than one thiosulphuric acid or thiosulphate group are curable and can be used with advantage in textile finishing, for example in the pigment dyeing and printing of fibrous materials including pure synthetic fibres, in application to fibres or fabrics to impart shape stabilisation, in application to keratinous fabrics to impart shrink resist properties and for the flat setting and permanent creasing of fabrics, and to impart antistatic properties to fibres and filaments. Hair may be treated according to the invention to improve its handle and for permanent waving and setting.

36 Claims, No Drawings

POLYMER TREATMENT OF FIBROUS AND FILAMENTARY MATERIALS

The present invention relates to the treatment of fibrous and filamentary materials including living human hair with certain polymeric compounds containing thiosulphuric acid or thiosulphate groups.

The invention provides a process for the treatment of fibrous and filamentary materials which comprises applying thereto a polymeric compound containing at least one poly (oxyalkylene) chain and at least one thiosulphuric acid or thiosulphate group (hereinafter referred to as a Bunte Salt group). Compounds containing a single Bunte Salt group are water-soluble and may have surface active properties. Compounds having more than one, and especially more than two, Bunte Salt groups in addition to being water-soluble may also be surface active and can be cured to water-insoluble condensation products. Such curable resins can be used in textile finishing. For example they may be employed for the pigment dyeing and printing of fibrous materials such as wool fabrics, polyester fabrics, cellulosic fabrics and paper. When applied as textile finishing agents to cotton, rayon, polyamide or polyester fibres or fabrics they can impart shape stabilisation thereto. In addition they may also act as antistatic agents. When applied to keratinous fabrics they can impart shrink resist properties and additionally certain compounds can be used for flat setting and permanent creasing of the fabric. They may also be used for the treatment of living human hair. Because of their surface active properties they can be incorporated into shampoos and can impart to the hair an attractive handle. In addition they may be employed for the permanent waving or setting of hair.

The preferred compounds for use in the present invention are curable and contain one or more polyoxyalkylene chains and substantially two or more Bunte Salt groups each bound through a linking group to a chain-terminating oxygen atom. A preferred group of such compounds comprises:

a. a radical of a polyhydric alcohol;
b. bound to this radical at least two poly (oxyalkylene) chains; and
c. at least two Bunte Salt groups each bound through a linking group to a chain-terminating oxygen atom. Compounds wherein the linking group comprises an alkylenecarbonyl group are novel per se and are described and claimed in our Application No.

Compounds of especial interest contain three polyoxyalkylene chains and up to three Bunte Salt groups per molecule and have molecular weights in the range 500–10,000 especially 1,500–5,000. The linking groups may be the same or different in different poly (oxyalkylene) chains, and may be, for example, alkylene chains which may contain from 1 to 6 carbon atoms and may be unsubstituted or substituted with, for example, one or more hydroxyl groups. The linking groups may also be divalent acyl radicals of carboxylic acids. The compounds of the invention may also contain free hydroxyl or thiol groups or polyoxyalkylene chains linked together by thioether or disulphide bridges.

Compounds which may be employed are represented by the general formula:

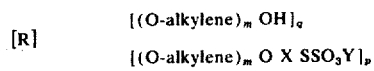

or by the general formula

wherein
p is an integer from 2 to 6;
q is 0 or an integer from 1 to 4 subject to the proviso that (p+q) is in the range 3 to 6;
m is an integer of value at least 1 (most usually from 5 to 25) and may have different values in each of the p and q chains;
R represents a radical formed by removal of the hydroxyl groups from an aliphatic polyhydric alcohol containing at least two carbon atoms. Each 'alkylene' group contains a chain of at least 2 and at most 6 carbon atoms between consecutive oxygen atoms;
X represents a divalent group containing 1 to 10 carbon atoms;
Y represents a hydrogen atom or a salt forming ion or group The preferred compounds are of formula

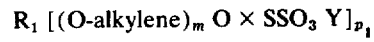

wherein m, X and Y are as defined in formula I,
R represents a radical derived from an aliphatic alcohol containing from 3 to 6 carbon atoms and from 3 to 6 hydroxyl groups and $p_1$ is an integer from 3 to 6.

The compounds which may be employed may also contain disulphide linkages between polyoxyalkylene chains. Where the linkage is between chains attached to different groups $R_1$ the compounds may be of the formula IV.

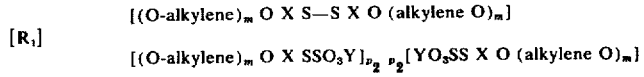

wherein $R_1$ has the meaning given in formula III, alkylene, m, X and Y have the meaning given in formula I and $p_2$ represents an integer from 2 to 5. The compounds may also contain disulphide linkages between polyexyalkylene chains bound to the same group $R_1$ and in this case may be of the general formula V

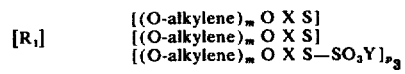

wherein $R_1$ has the meaning given in formula III, m and alkylene have the same meanings as in formula I and $p_3$ represents an integer from 1 to 4.

The group R represents a radical formed by notional removal of the hydroxyl groups from an aliphatic polyhydric alcohol. Suitable radicals are, for example, those derived from ethylene glycol, propylene glycol, cyclohexane, 1,4-diol, 1,1,1-trimethylolethane, 1,1,1-trimethylolpropane, pentaerythritol and sucrose. The group R may also comprise a hydroxy terminated adduct of an adduct of one or more alkylene oxides with ammonia or an amine, examples of such compounds being the propylene oxide adducts of ammonia, ethylenediamine; or triethanolamine. Preferably R is derived from an alcohol containing three hydroxyl groups, and the preferred radical is derived from glycerol.

The alkylene groups may be $C_2H_4$, $C_3H_6$, or $C_4H_8$ radicals. Compounds containing $C_3H_6$ and/or $C_4H_8$ radicals are hydrophobic and the Bunte Salt compounds derived therefrom act as surface active agents.

The compounds may for example contain mixtures of $C_2H_4$ and $C_3H_6$ derived groups and may be random or block copolymers. The surface tension properties may be adjusted by selection of the ratio of $C_2H_4$ to $C_3H_6$ radicals. For example a suitable triol may be formed as a block copolymer by condensing glycerol with propylene oxide and "tipping" the resulting triol with ethylene oxide.

Condensation products of glycerol and ethylene oxide and/or propylene oxide are available commercially, for example those sold under the trade names Polyurax (B.P. Chemicals), Caradol (Shell Chemical Co) and Propylan (Lancro Chemicals Ltd.).

The group X is preferably a substituted or unsubstituted divalent aliphatic radical and may for example be of the formula

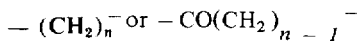

where $n$ is an integer of 1 to 6, or may be of the formula

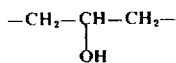

Compounds of especial interest have molecular weights in the range 1,500 – 5,000 and are of the formula

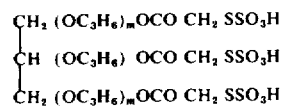     VI wherein $m$ has the same meaning as in formula I. Water soluble salts, for example the alkali metal (especially sodium), ammonium or amine salts may also be used. Other useful compounds of molecular weight 1,500 – 5,000 are of the formula

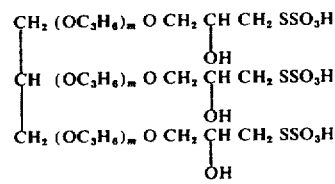     VII or their alkali metal (especially sodium), ammonium or amine salts.

Another preferred group of resins which can be used are derived from aliphatic polyamide/epichlorohydrin resins. Such resins may be prepared by
a. condensing a dicarboxylic acid with a polyamine containing at least two primary amino groups and at least one secondary amino group;
b. reacting the condensate with a compound capable of introducing hydroxyazetidinium ions, N-glycidyl groups or groups containing replaceable chlorine atoms; and
c. reacting the product with a water-soluble thiosulphate.

Preparative Methods

Polymeric compounds for use in the present invention may be prepared by esterifying an alcohol containing at least one poly(oxyalkylene) chain and at least two terminal hydroxyl groups with a halogen substituted carboxylic acid or functional derivative thereof and reacting the resulting halogeno-ester with a water soluble thiosulphate. If the alcohol is of the general formula $$[R][(O\text{-alkylene})_m OH]_{p+q}$$     VIII where R, alkylene, $m$, $p$ and $q$ have the meanings given above and is reacted with an acid $Cl(CH_2)_n COOH$ where $n$ is an integer of value 1 to 5 or a chloride or anhydride thereof there is produced an intermediate chloro compound of the general formula

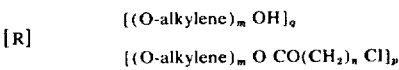     IX which reacts with a water-soluble thiosulphate to produce a compound of formula I wherein X represents a $-CO(CH_2)_n-$ residue.

The esterification reaction can conveniently be carried out by refluxing the polyol and the halogenocarboxylic acid in an organic solvent, for example toluene. A catalyst e.g. toluene - p - sulphonic acid is normally present and the water produced is distilled off and collected in a Dean and Stark trap. The chloro-ester so obtained can be converted to the Bunte Salt by reaction with sodium thiosulphate in an aqueous/alcoholic medium under reflux.

In an alternative method an alcohol containing at least one poly (oxyalkylene) chain and at least two terminal hydroxyl groups, for example a polyol of the general formula VIII can be reacted with an epihalohydrin, for example epichlorohydrin, followed by reacting the resulting epihalohydrin adduct with a base to produce an epoxy-terminated adduct with a water soluble thiosulphate. The polyol of general formula VII reacts with epichlorohydrin in the presence of $SnCl_4$ under reflux in an organic solvent such as toluene and subsequently with a base to produce a compound of the formula

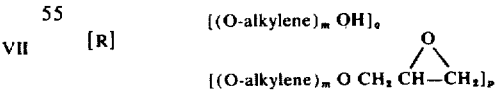     X wherein R, alkylene, $m$, $p$ and $q$ have the meanings previously assigned. This epoxy compound can readily be converted by treatment with sodium thiosulphate in an aqueous/alcoholic solvent into a compound of formula I wherein X represents a

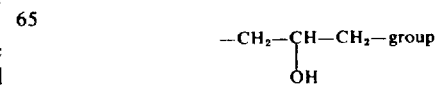

Compounds for use in the invention can also be produced by treatment of the corresponding thiol compounds with a water-soluble bisulphite and a water-soluble tetrathionate. Suitable thiol compounds have a. a radical containing at least one poly (oxyalkylene) chain and at least two chain terminating oxygen atoms notionally derived from terminal hydroxyl groups; and b. at least two thiol groups each bound through an alkylene, hydroxy-substituted alkylene or alkylcarbonyl group to a chain terminating oxygen atom.

Suitable thiols are of the general formula

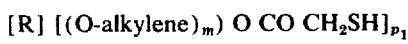

or of the formula

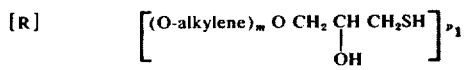

wherein R, alkylene and $m$ are defined in formula I and $p_1$ is an integer from 3 to 6.

The compounds of formula XI or XII can produce Bunte Salt terminated compounds of the general formula I on warming with sodium bisulphite and sodium tetrathionate in an aqueous/alcoholic medium. Suitable thiol-terminated starting materials are disclosed, for example, in British Pat. Specification No. 1,278,934. The reaction may also give rise to compounds containing disulphide linkages, such compounds being of the general formula IV or V. Normally these disulphide compounds, which are within the scope of the invention, are minor components of the reaction products.

In preparing the polyamide-based compounds the dicarboxylic acids which may be used as starting materials preferably contain 3 to 20 carbon atoms and contain saturated aliphatic (including cycloaliphatic) carbon atoms, and are reacted with a polyalkylene polyamine containing from 2 to 8 alkylene groups. Examples of suitable aliphatic dicarboxylic acids include malonic, succinic, adipic or azelaic acids and their amide forming derivatives such as dimethyl esters, or mixtures of such acids and esters. One or more polyamines can be used in the formation of these epichlorohydrinpolyamine resins; specific examples are diethylenetriamine, triethylenetetramine, tetraethylenepentamine, dipropylenetriamine, and N.N-bis (3-aminopropyl) methylamine. Suitable amines preferably contain at least 2 amino groups separated by a hydrocarbon group having the general formula $C_nH_{2n}$ where $n$ is at least 2. The condensation reaction can for example be represented by the equation $x$ moles HOOC(CH$_2$)$_4$—COOH + $x$ moles
H$_2$N(CH$_2$)$_2$NH(CH$_2$)$_2$NH$_2$ → HOOC(CH$_2$)$_4$CO
(NH(CH$_2$)$_2$NH(CH$_2$)$_2$NH.CO(CH$_2$)$_4$CO)$\alpha_7$NH(CH$_2$)$_2$
NH(CH )$_2$ NH$_2$ The product from step (a), which generally has a molecular weight of about 10,000, can then be treated with an epihalohydrib, dihalohydrin or an $\alpha$-, $\beta$-, or $\gamma$-halogen-carboxylic acid halide, for example chloroacetyl chloride, chloropropionyl chloride or chlorobutyryl chloride. The most preferred reagent is epichlorohydrin, and the precise structure of the amine-epichlorohydrin resins which are the corresponding products has been the subject of some controversy. It is believed, although the usefulness of this invention does not depend on the truth of this belief, that they contain hydroxyazetidinium ions

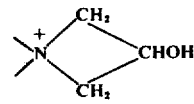

and/or N-chlorohydrin groups

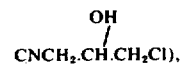

and/or N-glycidyl groups

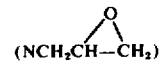

If chloroacetyl chloride is used, then the groups which are present will be

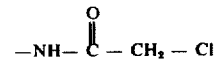

The polyamide/epichlorohydrin product of step (b) is a commercially available resin and is sold under the trade names "Hercosett 57", "Kymene 557" and "Alcoset".

The reaction with the water-soluble thiosulphate is carried out by adding to a solution of the product of step (b) an aqueous or aqueous/alcoholic solution of a water soluble thiosulphate, especially sodium thiosulphate, at a pH of 4 to 10 for a period of 1 to 24 hours depending on reaction temperature. If excess thiosulphate is employed the product separates as a lower phase of pale yellow colour, viscous and very soluble in water. The polyamide/epichlorohydrin resins give rise to side groups of the formula:

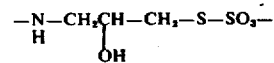

whereas the polyamide/chloroacetyl chloride resins give rise to side chains to the formula:

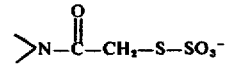

Suitable curable resins can also be produced by treating a protein, for example casein, with epichlorohydrin and subsequently treating the adduct formed with sodium thiosulphate to yield the thiosulphato curable resin.

Curing Reactions

Polymeric compounds containing substantially two or more Bunte Salt groups per molecule are curable and may be converted into insoluble cross-linked condensation products. It has been found that when preparing the compounds by substitution of terminal haloatoms, substitutions of about 60% give satisfactory curable products. The resins cure on prolonged exposure to light or heating. Curing is effected by treatment with acids, bases or reducing agents. Suitable reducing agents include quaternary phosphonium compounds, for example THPC (tetrakis-(hydroxymethyl)phosphonium chloride), sodium borohydride, thioglycollic acid and thiol-containing compounds such as thioethanol, cysteine, thioglycerol and resins containing free thiol groups such, for example, as those mentioned in British Pat. Specification No. 1,278,934. Curing may also be assisted by nucleophilic substances such as thiourea, nitrous acid, acid hypochlorite, iodide ions or thiocyanate ions. Curing may also be promoted by diamines, for example ethylene diamine, diethylene triamine, 1,6-diaminohexane or piperazine, especially with compounds of the formula $R-O-CO-CH_2-SSO_3Na^+$ or $R-NH-CO-CH_2SSO_3 Na^+$. In addition, tertiary amines may promote curing.

The compounds may be insolubilised by treatment with polyvalent metal ions, for example magnesium ions, and it may be advantageous to treat the resins in this way and simultaneously or subsequently treat them with a curing agent.

Textile Applications

In one aspect the invention provides a process for the treatment of textile material which comprises applying thereto a compound containing at least one poly (oxyalkylene) chain and at least two Bunte Salt groups and curing the resin on the material. The compound may be of any of the general formulae I to VII and from 0.1 to 15% of the resin, preferably 0.5 – 5% kg weight on the weight of material can conveniently be applied. The invention also consists in textile fibres, especially wool fibres, bearing a deposit of a cured resin as defined herein and/or of any one of the general formulae I to VII.

The compounds may be applied to synthetic fibres, for example polyamide, polyester or acrylic fibres and impart an attractive handle thereto. In addition they may also act as antistatic agents. The compounds may be applied to natural or regenerated cellulosic fibres and can impart wrinkle resist and permanent press properties thereto. They may act as pigment binding agents and can be employed in the pigment dyeing or printing of natural regenerated and synthetic fibrous or filamentary materials.

The compounds are of especial value for the treatment of keratinous textile materials, usually derived from the wool of sheep, or from alpaca, cashmere, mohair, vicuna, guanaco, camel hair or llama or blends of these materials with sheep's wool. The treatment of such materials according to the invention can be used to impart shrink-resist and/or permanent press properties thereto. The wool may be mixed with other textile fibres, for example polyamide, polyester or cellulosic fibres but in the shrink-resist treatment of wool-containing fabrics generally at least 30% of the material is wool, and wool rich blends, for example 60:40 wool/cotton blends, 80:20 wool/nylon blends and 80:20 wool/polyester blends may be used.

The compounds may be applied to the textile material by any conventional technique, for example by padding or by exhaustion from a dyebath. In the treatment of wool the resins have the advantage that they are anionic and are compatible with wool dyes which normally contain anionic solubilising groups. Thus acid levelling, acid milling, premetallised and solubilised vat dyes can be used but for best dye fastness to washing it is preferred to use fibre-reactive dyes, i.e. dyes that can react with the keratin fibre and become covalently bonded thereto. The acid levelling dyestuffs can be, for example of the azo type and should be water soluble and contain at least one anionic solubilising group, generally a sulphonic acid group. Acid milling dyes generally have a greater molecular weight and fewer solubilising gruops than the acid levelling dyes, but there is no rigid distinction between the two classes. The premetallised dyes comprise a class of dyes having 0.0' - dihydroxy azo, o-amino-o'-hydroxy azo or o-carbonyl-o'-hydroxy azo groups which are co-ordinated to a metal atom, for example chromium or cobalt. The dyes may be used as 1:1 or 2:1 complexes. Vat dyes, which are most commonly of the indigoid or anthraquinone structure, are solubilised by conversion to their water-soluble leuco esters and can subsequently be developed after application by oxidation to the insoluble form. It has also been found that pigments can be applied to wool fibres by pad dyeing or printing in the presence of the resins herein described, and that the resulting pigment dyed or printed materials have high wash and rub fastness.

The process is especially advantageous when combined with dyeing with an aqueous solution of water-soluble wool dye. Previously shrinkproofing resins have been found to be incompatible with reactive dyes owing either to the formation of ion complexes or to their water-insolubility. A preferred process for dyeing with such a dye comprises impregnating the fibres at a pH of 5–12 with an aqueous composition comprising a reactive dye and a water-soluble polymer comprising thiosulphuric acid or thiosulphate groups, a reducing agent for the keratin and an additive for facilitating penetration of the dye into the keratin fibres, storing the dyed and polymer-treated fibres in the presence of moisture to allow penetration of the dye into the fibres and deposition of the resin thereon, and thereafter subjecting the fibres to a washing treatment. If necessary the washing solution may contain 0.1–2.0% by weight of a curing agent for the resin.

When producing shades on wool or similar materials by a method of impregnation followed by storage, it is possible, if desired, to add to the dye liquor a further surfactant which produces rapid wetting of the wool at room temperature. These additives are exemplified by non-ionic condensation products of e.g. lauryl diethanolamide. The anionic Bunte Salts can themselves serve as wetting agents.

The reactive dyes which may be employed also include whitening agents which react with fibres in the same way. Dyestuffs falling within this class can incorporate the following groups:

epoxy-, ethylene-imino-, isocyanate, isothiocyanate, carbamic acid aryl-ester-, propiolic acid amino, monochloro- and dichloro-crotonylamino, chloroacrylamino-, acrylamino, sulpho halo, sulphuric acid ester, sulphonyloxy-, thiosulphato, labile halo atoms, trichloro-pyridazino-, dichloroquinoxalino-, allysulphonyl-, monochlorotriazinyl-, vinylsulphonyl-, and certain reactive ammonium or hydrazinium residues.

The process of dyeing according to the invention is applicable by pad-dyeing. Especially good results in pad-dyeing are obtained with highly reactive dyes, for example those incorporating a 2,4-dichlorotriazinyl, 2,3-dichloroquinoxaline, 2-chloro - 4 methoxytriazinyl, 2,4-dichloro - 5 - carbonylpyrimidine or 2,4 - difluoro - 5 -chloro-pyrimidine group.

Reducing agents are preferably incorporated into the pad liquor, and examples include alkali metal, ammonium and amine sulphites and bisulphites, for example, sodium bisulphite, sodium metabisulphite, and monoethanolamine bisulphite, certain quaternary phosphonium compounds, for example, tetrakis-(hydroxymethyl) - phosphonium chloride, sodium borohydride, and thioglycollic acid and other materials capable of breaking disulphide bonds in the keratin molecule. The amount of reducing agent per 100 parts by weight of paste may for example be from 1 to 50, preferably from 1 to 20 parts by weight. Sodium bisulphite is preferred and has the advantage that it exerts a bleaching action on the wool and therefore allows very bright shades to be obtained, and also appears to promote reaction between the wool and the resin.

It is preferred to include an additive in the pad liquor to assist penetration of the dye into the keratin fibres. While the invention does not depend on any theory as to its mode of action, it is believed that the additive can cause swelling of the keratin fibre and/or disaggregation of the dyestuff. Suitable additives include acid amines or thioamides, for example urea, thiourea, sulphamide, or derivatives thereof, furfuraldehyde and cinnamaldehyde, and the additive is preferably present in the aqueous composition in a concentration of 100 – 400 grams per litre, especially in the case of urea about 300 g/l.

The simultaneous dyeing and resin treatment can be carried out by dissolving the reactive dye and the resin in water, preferably in the presence of an acid amide or thioamide, for example urea, and in the presence of a reducing agent for the keratin, for example sodium bisulphite, and subsequently impregnating the fibres with the dye composition for example, by impregnation with a pad mangle. The process can be carried out at ambient temperatures or from 10° to 60°C although slightly elevated temperatures, preferably below 50°C, are best. The dyeing can be carried out at a pH in the range 2–12 but is preferably conducted at a pH of about 10. The fibres are allowed to remain in contact with the dye for the minimum time for proper penetration, e.g. between 10 mins. and 72 hrs, typically between 1 and 24 hours. For example, the fibres may be removed, squeezed to express excess liquid and then stored in the presence of moisture for 10 mins. to 72 hrs to ensure that the bulk of resin and of the dye becomes attached to the keratinous fibres leading to a full shade development of the dye. After the storage period the fibres may be washed off with a solution of a curing agent, for example a mixture of magnesium chloride and ammonium thioglycollate and optionally are subsequently treated with an aqueous solution of a base. Conventional equipment can be used for applying these solutions, for example, a beam washer, a winch or a conventional washing range.

Pigment Dyeing

The resins of the invention can be used to advantage in the production of fast dyed shades on all fibres using pigments. Pigments are generally classified as water insoluble colours and their current use on textile materials is limited by the following restrictions:

i. Pale depths only can be achieved due to the poor rub fastness of deeper shades.
ii. A pigment dyeing or print always appears 'glassy' to the trained observer.
iii. Usually up to 10% o.w.f. polymer binder is employed which has a very great effect on harshening the 'handle' of the material.

The use of the Bunte Salt polymers either alone or in a mixture completely eliminates the above problems and allows the production of a wide range of satisfactory shades on all fibres by printing or dyeing. Printing or dyeing is carried out with a mixture of the Bunte Salt polymer, pigment and thickener followed by a curing step which may be a simple cold rinse in a solution of reducing agent or diamine, or which may be a heat curing step carried out for example for 5 minutes at 140°C. Washing in cold water completes these processes.

One great advantage of the pigment dyeing procedure is that solid shades can be achieved on wool/synthetic fibre blends. Other advantages include the shrink proofing effect imparted to wool and the antistatic effects and wrinkle resistance imparted to such fibres as polyester cotton.

Treatment of Hair

It has been found that the process of this invention can be employed for the treatment of hair, including living human hair.

The polymeric compounds defined above can be formulated into a composition for the treatment of hair comprising the polymeric compound and at least one inert solvent or diluent. Such compositions provide a further aspect of the invention. Preferably the composition contains from 0.5 to 15% by weight, preferably from 2 to 6% by weight, of the polymeric compound. The composition preferably also contains a reducing agent for the keratin (other than a curing agent for the polymer), for example sodium bisulphite, and optionally also a nucleophilic substance such as thiourea. The reducing agent is conveniently present in an amount of from 0.2 to 10% by weight based on the weight of the composition. In order that the composition should have satisfactory storage stability it preferably contains at least 20% by weight of water and is adjusted to pH in the range 3–10, preferably about 7. The composition may be in the form of an aqueous or aqueous/alcoholic silution and may be, for example, in the form of a shampoo or wave-setting lotion. It may alternatively be in the form of a cream or gel, the resin being dissolved in the aqueous phase thereof. The composition may contain any other conventional ingredient for use in cosmetics provided that the ingredient does not react with Bunte Salts. For example the composition may additionally contain one or more surfactants, hair dyes, pigments, perfumes, swelling agents or thickening agents. The composition may also be formulated as an aerosol.

In a further aspect the present invention provides a process for the treatment of hair, including living human hair, which comprises applying thereto a curable water-soluble polymer containing at least one poly (oxyalkylene) chain and two or more thiosulphuric acid or thiosulphate groups and curing the polymer on the hair. The polymeric compounds when applied to hair can enhance the appearance by making it brighter and may also facilitate combing out of the hair. When the hair has become degraded by the action of, for example, sea water, sunlight, bleaching agents or permanent waving agents, the compounds may have the effect of increasing the strength thereof. The compounds may also be used for the shape stabilisation of hair and are therefore of value for incorporation into permanent waving compositions. The hair may be formed into the desired shape or configuration, a solution of the resin is applied thereto and the polymer is subsequently cured.

The compounds can be applied to the hair by any conventional method, for example by brushing, spraying or dipping, and preferably remain in contact with the hair for a period of 5-30 minutes. The hair is then rinsed with an aqueous solution of a curing agent, for example a mixture of ammonium thioglycollate and magnesium chloride.

The invention is illustrated by the following Examples in which Examples I to VI, XXVI and XXVII relate to the preparation of resins for use in the method of the invention and Examples VII to XXV and XXVIII to XXXII are Examples of the invention.

EXAMPLE I

A polythiol was prepared from a mixture of 800 g (0.2 g-mol). of a triol of average molecular weight 4,000 made from glycerol and propylene oxide, 55.2 g (0.6 g-mol.) of thioglycollic acid, 5 g of toluene-p-sulphonic acid and 350 ml of toluene by heating to reflux with stirring in an atmosphere of nitrogen. Water (10.8 ml, 0.6 g-mol.) formed during the reaction was removed as its azetrope with toluene. The mixture was cooled and washed with water, and the organic layer was separated. On removal under vacuum of the solvent from the organic layer there remained 793 g (94% of the theoretical yield) of the desired tris(thioglycollate) having a thiol content of 0.59 equiv./kg.

The above polythiol resin (1 mole) was treated with sodium bisulphite (4 moles) in water and isopropanol was added to the liquor until a clear solution was obtained. The solution was heated to 60°C for 4 hours and sodium tetrathionate ($Na_2S_4O_6$, 2 moles) was added, the solution then being maintained at 60°C for a further hour. A further 4 moles of sodium bisulphite and 2 moles sodium tetrathionate were then added as before. A yellow oil separated from the solution and was discarded. The solution was cooled and allowed to stand overnight, and the solvent was evaporated off in vacuo to give a clear, viscous, curable, organic resin which was soluble in water and exhibited surface active properties, and the infrared spectrum of the product showed bands characteristic of Bunte Salt groups at 1,030 cm$^{-1}$ and 1,050–1,190 cm$^{-1}$. The product was anionic and readily precipitated when treated with the blue basic dye Basacryl Blue XRL CCI Basic Blue 79). White precipitates of cured resin formed readily on treatment with hydrochloric or sulphuric acid, magnesium chloride, THPC or ammonium thioglycollate, and at pH 2.0 with thioglycollic acid in the presence of tertiary amines or thiourea. Boiling in dilute mineral acids produced the corresponding insoluble thiols, but disulphides can be formed under these conditions if thiourea is present.

EXAMPLE II

A triol (100g) of average molecular weight 3,000 prepared by condensation of glycerol with propylene oxide (Polyurax G3000, B.P.Chemicals Ltd) was dissolved in toluene (300 ml). Chloroacetic acid (15 g) was added together with toluene p-sulphonic acid (5 g). The mixture was refluxed for 4 hours at 110°C in an atmosphere of nitrogen and the water liberated was collected as its azeotrope with toluene in a Dean and Stark apparatus. The theoretical yield of water (1.8 ml) was recovered. The reaction mixture was washed with water and sodium bicarbonate (1% w/v) several times to remove excess chloroacetic acid and catalyst, and the toluene was removed by rotary vacuum evaporation. The residual tris-chloroacetyl ester (95 g) was dissolved in isopropanol (300 ml) and sodium thiosulphate pentahydrate (30 g) in water (50 ml) was added. Isopropanol and water were subsequently added as required to maintain a clear solution, together with acetic acid to bring the pH to 5.0. Refluxing was carried out for 4 hours at 80°C with stirring and at the end of this time a sample of the reaction liquor dissolved in water without turbidity. The solution was cooled and allowed to stand for 10 hours after which it was observed that separation into two phases had occurred. The upper resin phase was separated from the lower aqueous phase which contained a high proportion of dissolved salt. The resin phase was evaporated down in vacuo to give a clear viscous resinous material (92 g) which was readily soluble in water and exhibited surface active properties. The infra-red spectrum exhibited bands of 1,030 and 1,050–1190 cm$^{-1}$ characteristic of Bunte Salt groups. Estimation of the Bunte Salt groups by conversion to thiol groups and subsequent titration indicated the presence of three Bunte Salt groups per molecule.

The reaction is believed to take place as follows:

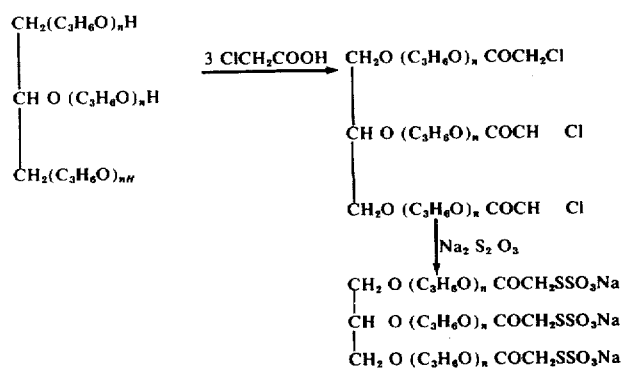

In like manner Bunte Salt resins were prepared from the following polyol starting materials:- Propylan G 1000, G 1500, G 3000, G 4000 and G 5000 (Lancro Chemicals Ltd) and Voranol CP 700 (Dow Chemical Co), the figures indicating the molecular weight of the polyol.

EXAMPLE III

The resin prepared in Example II decomposed over the course of a few days when allowed to stand. A composition which could be stored for prolonged periods was prepared by diluting the evaporated product with water until the solids content was 80%, and adding a buffer(disodium hydrogen phosphate) to maintain the pH at about 7. The resulting concentrated solution was stored for a period of several months without noticeable deterioration.

EXAMPLE IV

Polyurax G 3,000 (100 g) was dissolved in toluene (100 ml) and stannic chloride (0.4 g) was added. Epichlorohydrin (12 g) was then added and the mixture was refluxed for 2 hours at 110°C. The solution was cooled and washed with a solution of sodium hydroxide at pH 12. The organic phase was evaporated to dryness on a rotary vacuum evaporator and the resulting epoxy-terminated resin was dissolved in isopropanol(200 ml A solution of sodium thiosulphate pentahydrate (30 g) in water (50 ml) was added. Further isopropanol and water were then added as necessary to give a clear solution. The pH was adjusted to 7.0 and the mixture was refluxed for 4 hours. During this period a little dilute acid was added as necessary to maintain the pH at 7.0. The mixture was cooled and allowed to stand overnight. The mixture was observed to have separated into two layers, the upper of which contained a resin similar to that prepared in Examples I and II. The upper layer was separated and solvent was removed by rotary vacuum evaporation. The resulting pale yellow resin was water soluble and surface active. Its infra-red spectrum showed bands attributable to Bunte Salt groups.

A stable aqueous concentrate of the resin was prepared as described in Example III.

The reaction is believed to be as follows:

refluxed for 1 hour after which a precipitate of sodium chloride was noted, the product now being in the form of the tris($\beta$-iodopropionyl ester). Sodium thiosulphate pentahydrate (70 g) in water (100 ml) was added and the mixture was refluxed for 6 hours. At the end of this time a sample of the mixture when added to water was completely miscible and no turbidity appeared. The mixture was cooled and allowed to stand overnight. It separated into two phases of which the upper phase contained a pale yellow curable resin which was readily soluble in water, exhibited surface active properties, and gave an immediate precipitate with THPC. The product is believed to be

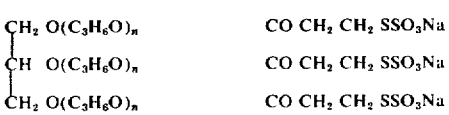

The remaining ester portion was similarly treated, but without iodide catalysis; no Bunte Salt was formed.

EXAMPLE VI

A diol of molecular weight approximately 2,000 containing propylene oxide derived units (Propylan D 2,112 Lankro Chemicals Ltd.) (212 g.) was dissolved in toluene (150 ml) and chloracetic acid (50 g) and toluene p-sulphonic acid (12 g) were added. The mixture was refluxed for 1 hour at 125°C and cooled. The excess acid was removed by stirring with sodium car-

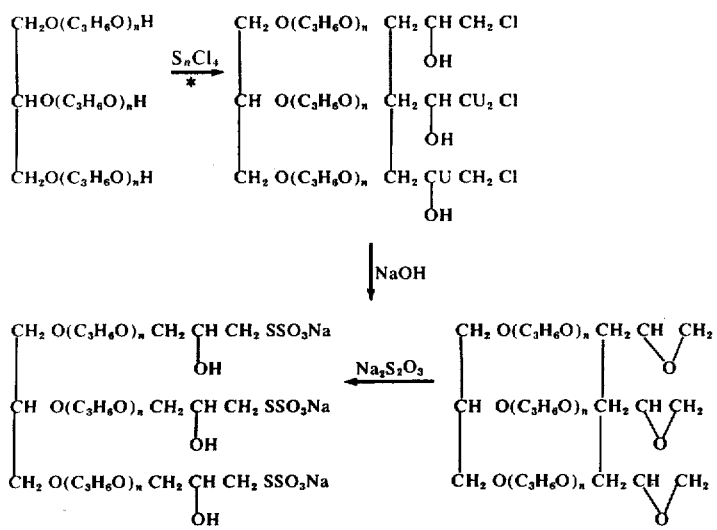

*in the presence of epichlorhydrin

EXAMPLE V

Propylan 3 (300g), glycerol/propylene oxide condensation product of molecular weight 3000, was dissolved on toluene (300 ml) and $\beta$-chloropropionic acid (80 g) and toluene p-sulphonic acid (15 g) were added. The mixture was refluxed for 5 hours at 110°C and the expected 5.4 ml of water was distilled off and collected at its azeotrope with toluene in a Dean and Stark trap. The mixture was cooled, washed with aqueous sodium bicarbonate and the resulting tris($\beta$-chloropropionyl) ester was recovered by evaporation. A portion of the ester (200 g) was dissolved in ethanol (200 ml) and potassium iodide (12 g) was added. The mixture was bonate (30 g) in water (500 ml) for 1 hour. The organic layer was separated and the dissolved ester was recovered by evaporation.

The ester was dissolved in isopropyl alcohol (200 ml) and sodium thiosulphate pentahydrate (170 g) in water (150 ml) was added. The mixture was refluxed for 2 hours, cooled and allowed to stand. Separation into 2 phases occurred, and the upper resin-containing phase was separated and concentrated as described in Example I. A water-soluble resin was obtained which exhibited surface active properties and gave an immediate precipitate with THPC. The infra-red spectrum of the product showed bands characteristic of Bunte Salt groups.

EXAMPLE VII

The following composition was applied by padding to a carbonised woollen flannel cloth and to worsted serge:-

| | |
|---|---|
| Resin of Example I | 30 g/l, corresponding to 3% on the weight of fabric(o.w.f,) |
| Urea | 300 g/l |
| Polysaccharide-base thickener (Guaranate AP5) | 6 g/l |
| Sodium metabisulphite | 20 litre |
| Procion Red MG (a reactive dye) | 20 g/l |

The material was wound up on a batch, covered with a polyethylene sheet and stored for 24 hours. It was then washed with water, then with a solution of aqueous ammonia (1cc 880 ammonia per liter) at 60°C for 15 minutes and then with dilute acetic acid. The area felting shrinkages determined after test washing in a 15 liter "Cubex" washing machine at 40°C and pH 7 at a 15:1 liquor:goods ratio are shown in Table I.

TABLE I

| Fabric | Resin treatment | pH | % AREA SHRINKAGE | | |
|---|---|---|---|---|---|
| | | | 1 hr. Wash | 2 hr. Wash | 3 hr. Wash |
| Worsted serge | Untreated | — | 32% | — | — |
| | As Example VII | 4 | 1% | 3% | 8% |
| Woollen flannel; scoured and milled (not carbonised | Untreated | 8% | 29% | 32% | |
| | As Example VII | 4 | 0% | 0% | 1% |

EXAMPLE VIII

A wool serge fabric was treated by padding to the wet pick up indicated in the following Table with the following liquor.

| | |
|---|---|
| Resin of Example II | 38 g/l |
| Urea | 300 g/l |
| Procion Red Mg Cl Reactive Red 5 | 100 g/l |
| Sodium bisulphite | 20 g/l |
| Guaranate AP 5 | 6 g/l |

The treated fabric was wound up, covered with a polyethylene sheet and stored for 24 hours at room temperature. It was then washed as indicated in Table II and the felting shrinkage was determined by washing as in Example VII. The results are shown in Table II in which "MgCl₂ wash" means a wash with a 2% aqueous solution of magnesium chloride at the indicated temperature and pH values followed by a wash with 0.5% aqueous ammonia for 15 minutes. It may be seen that the red dyed material exhibited a low felting shrinkage after washing, especially when treated with T.H.P.C. or magnesium chloride.

Some of the fabric treated in the above manner was sprayed with a solution of monoethanolamine bisulphite to give 2% solids on weight of wool and then creased in a hot steam press. This fabric was then tested for 3 hours by the above Cubex method and it was observed that no felting shrinkage occurred and that the crease remained completely intact. Thus the Bunte Salt resins are capable of imparting very high antifelting properties coupled with permanent press.

TABLE II

| Fabric | Wet Pick Up | % resin o.w.f. | Aftertreatment | % Area Shrinkage | | |
|---|---|---|---|---|---|---|
| | | | | 1 hr wash | 2 hr wash | 3 hr wash |
| Wool Serge | 130% | 4.9 | 0.5% aqueous ammonia | 11 | 24 | 40 |
| | | | 1% THPC (15 mins. 20°C) | 3 | 5 | 11 |
| | | | MgCl₂ wash (20°C, PH 5) | 2 | 4 | 2 |
| | | | MgCl₂ wash (20°C, PH 9) | 1 | 1 | 1 |
| | | | MgCl₂ wash (60°C, PH 5) | 1 | 1 | 2 |
| Uncarbonised Flannel, scoured and milled | 166% | 6.3 | 0.5% aqueous ammonia | 2 | 4 | 12 |
| | | | 1% THPC (15 mins. 20°C) | −1 | −2 | −2 |
| | | | MgCl₂ wash (20°C, pH 5) | 1 | 0 | 1 |
| Double Jersey | 129% | 4.9 | 0.5% aqueous ammonia | 2 | 4 | 12 |
| | | | 1% THPC (15 mins. 20°C) | 1 | 1 | 1 |
| | | | MgCl₂ wash (20°C, pH5) | | | |

One of the dyed and magnesium chloride aftertreated serge samples was exposed to the Xenotest accelerated fadeometer until Standard 6 on the Blue Scale had just started to fade. The fabric was then test washed as before and the results compared with an untreated sample.

| Sample | % Area Felting Shrinkage | | |
|---|---|---|---|
| | 1 Hr Wash | 2 Hr Wash | 3 Hr Wash |
| Unexposed | −1 | 0 | 0 |
| Exposed | −1 | 0 | 0 |

There was therefore no substantial deterioration in the shrinkproofing effect observed with this sample on exposure to light.

EXAMPLE IX

A wool serge fabric was impregnated by padding with the following composition to a wet pick-up of 130% by weight on the weight of the fabric

| | |
|---|---|
| Urea | 300 g/l |
| Thioglycerol | 0 g/l or 5 g/l |
| Resin of Example IV | 50 g/l |
| Sodium bisulphite | 20 g/l |
| Guaranate AP 5 | 6 g/l |
| Procion Red MG | 20 g/l |

The impregnated fabric was stored for 24 hours as in Example VIII and then washed in an aqueous magnesium chloride solution for 15 minutes at 60°C. The resulting red dyed fabric showed the following shrink resist results on test washing as before

| | % Area Felting Shrinkage | | |
|---|---|---|---|
| | 1 hour wash | 2 hour wash | 3 hour wash |
| UNTREATED | 45% | — | — |
| WITHOUT THIOGLYCEROL | 9% | 19% | 26% |
| WITH THIOGLYCEROL | 0% | 5% | 8% |

EXAMPLE X

A worsted serge fabric was padded to 100% wet pick up with a solution containing

| | |
|---|---|
| Resin of Example II | 4% o.w.f. |
| Sodium bisulphite | 10 g/l |
| Thiourea | 20 g/l |
| Sodium Carbonate | to give pH 8 |

After padding the fabric was rinsed with an aqueous solution of 2% v/v magnesium chloride and 2% v/v ammonium thioglycollate adjusted to pH 9, then with water, and then dried. A sample of the treated fabric exhibited about zero area felting shrinkage after 3 hours test washing.

EXAMPLE XI

Light Stability of the Polymers
Worsted serge was padded through the following pad liquors:

| | | |
|---|---|---|
| (i) | Polyol-based Bunte salt (80%) | 40 g/l |
| | Sodium Sulphite | 20 g/l |
| (ii) | As (i) but including Polyamide-based Bunte Salt (50% (for preparation see Example XXVI) | 20 g/l |

Immediately after padding the fabrics were cured in the following solutions for 10 minutes at 20°C.
a. Ammonium thioglycollate (2% w/v) Mg Cl$_2$ 6H$_2$O (2% w/v),
b. Hexamethylene diamine (2% w/v) NaCl (5% w/v). passed well with water and dried. Samples from these experiments were then exposed for 72 hours in the Xenotest machine, an exposure time, in fact, sufficient to fade the blue standard number 6 on the Blue Wool Scale. The exposed and non-exposed samples were then wash-tested for shrink resistance as before. The results are shown in Table III.

TABLE III

| Pad Liquor | After Treatment | light Exposure | % AREA SHRINKAGE | | |
|---|---|---|---|---|---|
| | | | 1 hr. | 2 hr. | 3 hr. |
| (i) | a | No | 0 | 0 | 0 |
| (i) | a | Yes | 9 | 22 | 25 |
| (i) | b | No | 0 | 1 | 1 |
| (i) | b | Yes | 7 | 10 | 17 |
| (ii) | a | No | −1 | −1 | −1 |
| (ii) | a | Yes | 0 | 0 | 0 |
| (ii) | b | No | −1 | 0 | 0 |
| (ii) | b | Yes | 0 | 1 | 2 |

It is evident from this table that the use of the polyamide-based Bunte Salt improves the stability of the cured fabric to light.

EXAMPLE XII

Wool serge samples (a) without pretreatment, (b) pretreated with 5% o.w.f. THPC or (c) pretreated with 10 g/l ammonium thioglycollate were treated by exhaustion in a bath at a liquor:goods ratio of 30:1 with Glaubers Salt (10% o.w.f.), formic acid (1% o.w.f.) and the resin of Example II (4% o.w.f.). The bath was raised to the boil over a period of 1 hour and maintained at the boil for a further 30 minutes. Each sample was then divided into two portions, one of which was not treated further, while the other half was washed for 15 minutes at ambient temperature with aqueous magnesium chloride (2%) solution, adjusted by addition of ammonia to pH 9. The samples were tested for felting shrinkage by washing as previously described. The results obtained are shown in Table IV.

The method was repeated except that Lanasol Blue 3R (CI Reactive Blue 50) (2% o.w.f.) and an amphoteric levelling agent containing ethylene oxide derived groups, Albegal B, (1% o.w.f.) were included in the resin treatment liquor. An excellent dyeing was obtained and the fabric had good shrink resist properties.

TABLE IV

| FABRIC | AFTERTREAT-MENT | % AREA FELTING SHRINKAGE | | |
|---|---|---|---|---|
| | | 1 hr. Wash | 2 hr. Wash | 3 hr. Wash |
| Untreated | — | 45 | — | — |
| Pretreated with 3% owf THPC | Nil | 9 | 15 | 24 |
| | Nil | 21 | 35 | 49 |
| Pretreated with 10 g/l ammonium thioglycollate | MgCl$_2$ wash | 3 | 4 | 5 |
| No pretreatment but resin treated | Nil | 22 | 49 | — |
| | MgCl$_2$ wash | 15 | 46 | — |

EXAMPLE XIII

Wool yarn was treated in a package dyeing machine for a period of 20 minutes with an aqueous solution containing 5% by weight on the weight of yarn of THPC and 15 g/l ammonium thioglycollate. An aqueous solution containing the following composition was then applied.

| | |
|---|---|
| Resin of Example I | 4% o.w.f. |
| Formic Acid | 1.5% o.w.f. |
| Glauber's Salt | 10% o.w.f. |
| Lanasol Blue 3R | 2% o.w.f. |

After 2 hours the resin and dye were observed to have exhausted onto the yarn and an excellent blue dyed yarn having a high degree of resistance to felting shrinkage was obtained.

EXAMPLE XIV

A wool fabric was impregnated by padding with an aqueous composition containing the pigment dye Hostaperm Red E3B (CI Pigment Voilet 19) (1.5 g/l), the resin of Example II (50 g/l) and sodium bisulphite (10 g/l). The impregnated fabric was stored for 15 minutes and then washed in a dilute solution containing magnesium chloride and ammonium thioglycollate. A blue dyed fabric was obtained having good shrink resist properties. The pigment was well retained by the fabric and exhibited satisfactory fastness to washing, light and mechanical abrasion.

EXAMPLE XV

A sample of bleached human hair was treated with an aqueous composition comprising

| | |
|---|---|
| Resin of Example II | 20 g/l |
| Sodium bisulphite | 10 g/l |

The solution was allowed to remain in contact with the hair for 10 minutes, after which it was washed with a dilute aqueous solution containing ammonium thioglycollate and magnesium chloride. The hair was then allowed to dry. It was found to have an improved handle and gloss and was easier to disentangle on combing than the untreated hair.

EXAMPLE XVI

A sample of human hair was wound around a small diameter hair curler and treated with the aqueous composition of Example XV. The composition was allowed to remain in contact with the hair for 15 minutes at 40°C after which the hair was washed with a 2% by weight aqueous solution of magnesium chloride. The hair was then set in the usual way on a large diameter curler, washed with water and dried in a current of warm air. An excellent permanent curl was obtained which wasy very resistant to washing. The test was repeated in the absence of the resin, and the curl obtained was much less pronounced and less resistant to washing.

EXAMPLE XVII

A sample of human hair was impregnated with the following composition.

| | |
|---|---|
| Hostaperm Red E3B | 1.5 g/l |
| Resin of Example II | 50 g/l |
| Sodium bisulphite | 10 g/l |

Hostaperm Red is a pigment dye. The hair was immediately wound onto a small diameter hair curler and allowed to remain thereon for 16 minutes. It was then rinsed in a dilute aqueous solution of magnesium chloride and ammonium thioglycollate. The hair was dyed red and permanently curled. Both the curl and the dyeing were fast to washing. In the absence of the resin no dyeing is observed and the permanent waving is less pronounced and less fast to washing.

EXAMPLE XVIII

A print paste was prepared comprising

| | |
|---|---|
| Bunte Salt of Example II | 30 g/l |
| Hostaperm Red E3B | 6 g/l |
| Sodium sulphite | 10 g/l |
| Alginate/starch ether thickener | 50 g/l |

The above paste was applied by screen printing to a wool serge fabric and to cotton cloth, knitted polyester fabric, polyamide fabric and knitted acrylic fabric. Each fabric was then washed in saturated aqueous salt solution containing 2% ammonium thioglycollate for about 5 minutes at ambient temperatures. The fabric was washed in water and dried. In each case a bright red dyeing fast to washing, rubbing and dry-cleaning was obtained.

EXAMPLE XIX

A knitted double jersey Crimplene polyester fabric was printed with the following print pastes (1–3) to a 3-colour flowered design.
1. 50 g/l Bunte Salt concentrate of Example III 6 g/l Hostaperm Pink E (CI Pigment Red 122) 50 g/l of a 50:50 mixture starch ether: alginate thickness 10 g/l thiourea (adjusted paste to pH 9.0)
2. As 1 but using 12 g/l Helizarin Blue BT as pigment.
3. As 1 but using 3 g/l Helizarin Green GG as pigment.

After being printed the fabric was aftertreated for 5 minutes at 20°C in a saturated salt solution containing 2% (w/v) ammonium thioglycollate and then washed off in cold water and dried at 110°C. A very bright, clear print was produced, fast to washing, wet rubbing and light. The fastness to wet rubbing is particularly satisfactory in the deeper shades and is unexpectedly high for a print based on the use of pigment dyes.

EXAMPLES XX

The procedure of Example XIX was repeated except that the fabrics used were
a. 100% wool worsted
b. 100% nylon continuous filament knitwear
c. Triacetate continuous filament knitwear
d. Cotton woven poplin
e. 50:50 wool/polyester worsted In all cases fast prints of high wet rub fastness and lightfastness were produced.

EXAMPLE XXI

The procedure of Example XIX was followed except that curing was by a Thermosol treatment at 140°C for 5 mins. Again fast prints of high fastness were produced.

EXAMPLE XXII

The prints on 100% wool from Example XX were test washed for 3 hours at pH 7.0, and felting occurred only in the unprinted areas, producing an attractive seersucker effect.

This effect could be produced in the absence of colour by printing an unmilled woollen cloth in a floral design with the following paste:
50 g/l Bunte Salt concentrate of Example III
50 g/l of a 50:50 mixture starch ether/alignate thickener
20 g/l Sodium sulphite The fabric was cured by immersion for 10 minutes cold in a solution at pH 9.0 containing:
2% $MgCl_2$ w/v
2% ammonium thioglycollate followed by rinsing in cold water and drying.

The fabric was then milled in a 'Cherry Tree' milling machine in the presence of dilute acetic acid. An attractive floral effect was produced whereby the white printed floral areas had completely resisted milling and the weave structure was clear, but the unprinted areas had milled normally.

EXAMPLE XXIII

The following liquor was applied by padding to wool serge, polyester knitwear. wool/polyester knitted fabric and blended worsted and nylon knitwear to give 100% wet pick up in each case 6 g/l Hostaperm Red E3B
50 g/l Bunte salt concentrate from Example III
12 g/l Guaranate AP5
10 g/l Thiourea
Adjusted to pH 9.0

The fabrics were then cured as in Example XIX. An attractive dyeing, fast to light, wet rubbing and washing was achieved on all the above fabrics. It was noted that the coloration was solid on the wool/polyester blend fabrics.

EXAMPLE XXIV

Woollen fabric was padded with the following composition 50 g/l Bunte salt concentrate of Example III
5 g/l Sodium bicarbonate and dried for 5 mins at 130°C.

The fabric was then test washed for 3 hours and found to be resistant to felting.

EXAMPLE XXV

The following surface coating mixture was prepared

| | |
|---|---|
| Hostaperm Red E3B | 10 g/l |
| Bunte salt concentrate of Example III | 50 g/l |
| Hydroxyethylcellulose thickener | 20 g/l |
| Thiourea | 20 g/l |

The mixture was applied to wool and lead-primed metal surfaces. These materials were then heated for 10 minutes at 140°C. A bright red, water resistant coating was obtained on both materials.

EXAMPLE XXVI

Preparation of Bunte Salt Derivative of Hercosett 57

Sodium thiosulphate (40g) was added to 400 mls. of an aqueous solution of a polyamide/epichlorohydrin resin sold under the trade name Hercosett 57 (10% solids). A clear pale yellow solution was produced which was left to stand over-night, where upon it had separated into two phases. The more viscous lower phase (200mls) was separated from the upper phase.

The viscous phase was pale yellow in colour and very soluble in water. In addition it appeared to be very anionic in that it readily precipitated with the basic dye Basacryl Blue XRL (BASF) in marked contrast to Hercosett 57. Similarly the new resin was not precipitated by the anionic reactive dye Procion Red MG, in contrast to the ready precipitation of Hercosett 57.

The new resin is believed to the Bunte Salt derivative of the original polyamide/epichlorohydrin resin formed in the following manner

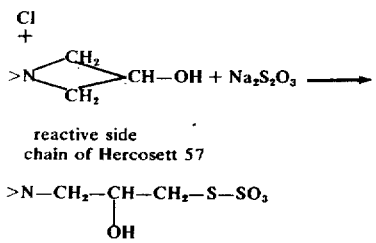

reactive side
chain of Hercosett 57

>N—CH$_2$—CH—CH$_2$—S—SO$_3$
        |
        OH

The observed chemical properties of the resin are summarised in the following Table.

| Aqueous Solution of | Reagent | Result |
|---|---|---|
| Bunte Salt polyamide | Thioglycollic Acid | Instant white Precipitate, insoluble in acids, alkalis and common organic solvents |
| Hercosett 57 | Thioglycollic Acid | No effect |
| Bunte Salt polyamide | Thioglycerol | White precipitate, insoluble in acids, alkalis and common organic solvents. |
| Hercosett 57 | Thioglycerol | No effect |
| Bunte Salt polyamide | H$_2$SO$_4$ (conc) in | Instant white precipitate insoluble — acids, alkalis and common organic solvents |
| Hercosett 57 | H$_2$SO$_4$ (conc) | No effect |
| Bunte Salt polyamide | THPC | Instant white precipitate |
| Hercosett 57 | THPC | No effect |

EXAMPLE XXVII

Preparation of a thiosulphato derivative of Gelatin

A suspension of gelatin (40g) in water (400 ml) was treated dropwise with epichlorohydrin (20 ml) at a temperature of 40° C with stirring. Addition took 15 minutes and the temperature was then raised to 60°C and maintained for 1 hour. The pH was maintained at 7.5 throughout this stage. The solution was then cooled to 40°C and acidified to pH 5 with acetic acid. A solution of 100 ml sodium thiosulphate (Na$_2$S$_2$O$_3$.5H$_2$O, 60.5 g) was added dropwise with the acetic acid during the reaction. The solution was allowed to stand overnight whereupon it separated into two phases. The lower phase was viscous and pale yellow in colour and contained a curable resin which exhibited the same reactions as the Hercosett derivative.

EXAMPLE XXVIII

The polyamide derived resin described above was applied to a prechlorinated knitted Boteny fabric having a cover factor of 1.1 using a pad mangle. The pad liquor contained the following substances.

| | |
|---|---|
| Procion Red MG | as specified |
| Urea | as specified |
| Guaranate AP5 | as specified |
| Sodium Metabisulphite | as specified |
| Dispersol VP | 10g/litre |
| Bunte salt resin (50% solids) | 60g/litre |

The concentrations of dye, urea, guaranate AP5 and sodium metabisulphite were varied and the effect of these variations is shown in the following table. In each case samples of the material were a) dried, b) batched and washed off with 1% aqueous solution of ammonia (normal wash off for pad-batch dyeing) or c) batched and washed off with a 1% solution of thioglycollic acid. Batch was carried out as follows: the dyed and resin treated fabric was wound up covered with polyethylene sheet and stored for a period of 24 hours. After treatments a), b) and c) above the fabric was then washed for 1 hour, 2 hours and 3 hours at pH7 in the presence of a detergent of 40°C in a Cubex washing machine with a liquor ratio of 15:1 to determine the felting shrinkage. The untreated fabric exhibited an area felting shrinkage of 47% in this test after washing for 1 hour. The results are shown in Table V. It is evident that samples given a reduction cure give excellent shrinkproofing. The necessity for a thickened liquor is also demonstrated.

The shrinkage results from the 15 litre Cubex test are given in Table VII.

TABLE V

| SAMPLE | UREA | SODIUM METABI-SULPHITE | GUARA-NATE AP5 | % AREA SHRINKAGE (1 hr. wash) | | |
|---|---|---|---|---|---|---|
| | | | | A. DRIED AFTER BATCHING | B. NORMAL WASH OFF | C. WASHED OFF 15 min 20°C in 1% SH.CH$_2$OOOH |
| 1. (a) No Dye in Liquor | 0g/l | 0g/l | 0g/l | 15 | 49 | 44 |
| b) 10g/l Dye | 0g/l | 0g/l | 0g/l | 30 | 36 | 32 |
| 2. a) No Dye in Liquor | 300g/l | 0g/l | 0g/l | 38 | 38 | 37 |
| b) 10g/l Dye | 300g/l | 0g/l | 0g/l | 41 | 43 | 44 |
| 3. a) No Dye in Liquor | 300g/l | 10g/l | 0g/l | 39 | 41 | 1 ( 2)* (9)** |
| b) 10g/l Dye | 300g/l | 10g/l | 0g/l | 30 | 44 | 15 |
| 4. a) No Dye in Liquor | 300g/l | 10g/l | 5g/l | 13 | 1(5)*(8)** | −2 (2)*(1)** |
| b) 10g/l Dye | 300g/l | 10g/l | 5g/l | 16 | 21 | 3 (6)* (12)** |
| 5. a) No Dye in Liquor | 300g/l | 0g/l | 5g/l | 22 | 38 | 4 (1)* (0)** |
| b) 10g/l Dye | 300g/l | 0g/l | 5g/l | 31 | 34 | 1 (13)* |
| 6. a) No Dye in Liquor | 0g/l | 10g/l | 5g/l | 39 | 33 | 0 (5)* (7)** |
| b) 10 g/l Dye | 0g/l | 10g/l | 5g/l | 27 | 37 | 3 (3)* (6)** |
| 7. a) No Dye in Liquor | 0g/l | 0g/l | 5g/l | 37 | 45 | 16 |
| b) 10g/l Dye | 0g/l | 0g/l | 5g/l | 33 | 42 | 15 |

*— 2 hr. wash
**— 3 hr. wash

EXAMPLE XXIX

A pad liquor was made up containing:-
60g/l Thiosulphate resin (50% solids) from Example XXVI
300g/l Urea
10g/l Dispersol VP Sodium Bisulphite
See Table
5g/l Guaranate AP5
10g/l Procion Red MG The pre-chlorinated wool knitwear of Example XXVIII was padded through the above bath and the material was batched for 24 hours at room temperature. The material was then washed in an aqueous solution containing THPC (1% v/v) for 15 minutes at 20°C. Shrinkage results were obtained from a 15 litre Cubex test and are given in Table VI.

TABLE VI

| | Chlorinated Knitwear % Area Shrinkage | | |
|---|---|---|---|
| 0g/l Bisulphite | 1 | (1)* | (1)** |
| 10g/l Bisulphite | 3 | (1)* | (2)** |
| | | * 2 hr Wash | |
| | | ** 3 hr Wash | |

EXAMPLE XXX

Pre-chlorinated wool knitwear was padded through a liquor identical to that used in Example XXIX, with the exception that 10g/l sodium bisulphite was included. The material was batched for 24 hours at 20°C and washed off as follows:

A. 1% (v/v) H$_2$SO$_4$ 15 mins., 20°C.
B. 1% (v/v) H$_2$SO$_4$ 15 mins., 50°C.

TABLE VII

| After-treatment | % Area Shrinkage | | |
|---|---|---|---|
| | 1hr. | 2hr. | 3hr. |
| A | 10 | — | — |
| B | 0 | 2 | 6 |

It is evident that sulphuric acid curing is more efficient at 50°C than at room temperature.

EXAMPLE XXXI

Using the pad liquor of Example XXX adjusted to pH10 with sodium carbonate the following fabrics were treated on a pad mangle with a dye/resin mixture, batched 24 hrs. at room temperature and subsequently washed off with a 1% aqueous solution of tetrakis-hydroxymethyl-phosphonium chloride. The treated fabrics were tested for shrink-resistance as in Example XXVIII. The fabrics treated were as follows:

1. Untreated botany single jersey.
2. A single jersey fabric which had been insufficiently piece chlorinated and which therefore gave pool shrinkage results at pH5 when pad-batch processed with Bunte Hercosett (compare with the excellent results previously obtained on top chlorinated fabrics).
3. Carbonised woolen, scoured and milled.
4. Wool serge.
5. Peroxide bleached yarns knitted into double jersey fabrics.
6. Scoured and milled flannel.
7. Dylan treated flannel.
8. Untreated double jersey.
9. Peroxide bleached worsted tropical.

The results are shown in the following Table (VIII).
It is evident that a great improvement in the washability of the fabrics is brought about by carrying out the process at pH10.

TABLE VIII

SHRINK RESIST RESULTS (15 l-Cubex)
Pad Liquor: 300g/l urea, 10g/l Dispersol VP, 5g/l Guaranate AP5, 10g/l Bisulphite
60g/l (3% o.w.f.) Hercosett Bunte Salt.
Curing: 1% THPC 15 min. 20°C.

| FABRIC | pH OF PAD LIQUOR | PROCION RED MG | % AREA SHRINKAGE | | |
|---|---|---|---|---|---|
| | | | 1 hr WASH | 2hr WASH | 3hr WASH |
| Untreated single jersey (No resin-area shrinkage 62%) | 5 | — | 50 | — | — |

TABLE VIII-continued

SHRINK RESIST RESULTS (15 1-Cubex)

Pad Liquor: 60g/l (3% o.w.f.) Hercosett Bunte Salt.
300g/l urea, 10g/l Dispersol VP, 5g/l Guaranate AP5, 10g/l Bisulphite Curing: 1% THPC 15 min. 20°C.

| FABRIC | pH OF PAD LIQUOR | PROCION RED MG | % AREA SHRINKAGE | | |
|---|---|---|---|---|---|
| | | | 1 hr WASH | 2hr WASH | 3hr WASH |
| (No resin-area shrinkage 62%) | 10 | — | 48 | — | — |
| Poorly chlorinated single jersey (No resin-area shrinkage 54%) | 5 | — | 2 | 17 | 37 |
| shrinkage 54%) | 10 | — | 1 | 2 | 4 |
| shrinkage 54%) | 10 | 10g/l | 1 | −1 | −1 |
| Carbonised Woollen scoured and milled (No resin-area shrinkage 14% (1hr), 22% (2hr), 30% (3hr) | 5 | — | 14 | 22 | — |
| 14% (1hr), 22% (2hr), 30% (3hr) | 10 | — | 0 | 2 | 5 |
| 14% (1hr), 22% (2hr), 30% (3hr) | 10 | 10g/l | 1 | 2 | 6 |
| Wool serge (No resin-area shrinkage 32%) | 5 | — | 29 | — | — |
| (No resin-area shrinkage 32%) | 10 | — | 16 | 34 | — |
| (No resin-area shrinkage 32%) | 10 | 10g/l | 13 | 28 | — |
| Peroxide bleached double jersey (No resin-area shrinkage) | 5 | 10g/l | 9 | 15 | 20 |
| 15% (1hr), 21% (2hr), 24% (3hr) | 10 | — | 3 | 7 | 7 |
| 15% (1hr), 21% (2hr), 24% (3hr) | 10 | 10g/l | 1 | 3 | 7 |
| Scoured and milled. (not carbonised) (No resin-area shrinkage) 19% (1hr), 29% (2hr), 32% (3hr) | 10 | 10g/l | 8 | 13 | 17 |
| Dylan, Carbonised scoured and milled (No resin-area shrinkage) 16% (1hr), 25% (2hr), 30% (3hr) | 10 | 10g/l | 4 | 7 | 10 |
| Untreated double jersey (No resin-area shrinkage 13% (1hr), 23% (2hr), 19% (3hr) | 10 | 10g/l | 9 | 14 | 19 |
| Peroxide Bleached Worsted Tropical (No resin-area shrinkage) 11% (1hr), 23% (2hr), 31% (3hr) | 10 | 10g/l | −1 | −1 | −1 |

EXAMPLE XXXII

The following aqueous composition was applied by padding to a carbonized woolen flannel cloth, a peroxide bleached double jersey fabric and a poorly chlorinated single jersey fabric.

| Urea | 300 g/litre |
| Dispersol VP | 10 g/litre |
| Guarnate AP5 | 5 g/litre |
| Gelatin derivative | 3% on the weight of fabric |

In some cases the pH of the composition was adjusted to 10 using aqueous sodium carbonate. The treated fabrics were stored for 24 hours, and then washed off for 15 minutes in a 1% solution of thioglycollic acid. The fabrics were then washed in a Cubex washing machine as described in Example XXVIII and the felting shrinkages were determined, and are shown in Table IX.

The process according to the invention can be applied successfully not only to natural fibres and to natural synthetic fibre blends, but also to pure synthetic fibres, e.g. polyester fibres. An important aspect of the invention is that it permits satisfactory pigment dyeing of synthetic fibres. Especially good results have been obtained with the pigment dyeing of polyester at ambient temperatures. The stability to light obtained by use together of polyol and polyamide/epichlorohydrin Bunte Salts is of importance (see Example XI).

TABLE IX

| Fabric | Pad liquor applied | pH | % AREA SHRINKAGE | | |
|---|---|---|---|---|---|
| | | | 1 hr. Wash | 2 hr. Wash | 3 hr. Wash |
| Carbonised Woollen Flannel | NIL | — | 14% | 22% | 30% |
| | YES | 4 | 10% | 20% | |
| | YES | 10 | 1% | 1% | 1% |
| Peroxide bleached double Jersey | NIL | — | 15% | 21% | 24% |
| | YES | 4 | 5% | 8% | 15% |
| | YES | 10 | 1% | 1% | 1% |
| Poorly chlorinated single Jersey | NIL | — | 54% | | |
| | YES | 4 | 0% | 0% | |

What I claim is:

1. A process for the treatment of fibrous or filamentary material which comprises applying thereto a polymeric compound comprising:
   a. a radical derived by the removal of two or more hydroxyl groups from a polyhydric alcohol;
   b. bound to this radical through an oxygen atom at the sites vacated by said hydroxyl groups at least two poly(oxyalkylene) chains; and
   c. at least two thiosulfuric acid or thiosulfate groups each bound through a linking group to a chain terminating oxygen atom of said poly(oxyalkylene) chains, said linking group containing from 1 to 10 carbon atoms and being an alkylene, alkylenecarbonyl or hydroxy alkylene group, and curing the compound on the fibres.

2. A process according to claim 1 wherein the polymeric compound has substantially three poly(oxyalkylene) chains and substantially three thiosulphuric acid or thiosulphate groups per molecule.

3. A process according to claim 1 wherein the polymeric compound has a molecular weight of 1,500–3,500.

4. A process according to claim 1 wherein the polymeric compound contains polyoxyalkylene chains linked together by thioether or disulphide bridges.

5. A process according to claim 1 wherein the polymeric compound has the formula

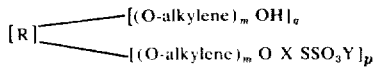

or the formula $$YO_3SSX — (O\text{-alkylene})_m —XSSO_3Y$$

wherein
- $p$ is from 2 to 6;
- $q$ is 0 to 4 subject to the proviso that $(p + q)$ is from 2 to 6;
- $m$ is at least 1 and may have different values in each of the $p$ and $q$ chains;
- R represents a radical formed by removal of the hydroxyl groups groups from an aliphatic alcohol containing at least two carbon atoms and at least two hydroxyl groups;
- each "alkylene" group contains a chain of from 2 to 6 carbon atoms between consecutive oxygen atoms;
- X represents said linking group; and
- Y represents a hydrogen atom or a salt-forming ion or group.

6. A process according to claim 5 wherein the compound has the general formula

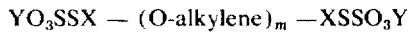

wherein $m$, X and Y and "alkylene" are as defined in claim 5, R represents a radical derived from an aliphatic alcohol containing 3–6 carbon atoms and 3–6 hydroxyl groups and $p_1$ is from 3 to 6.

7. A process according to claim 5 wherein R represents a residue derived from glycerol.

8. A process according to claim 5 wherein the alkylene groups comprise propylene groups or a mixture of ethylene and propylene groups.

9. A process according to claim 5 wherein X represents -C - (CH) - where n 1 to 6.

10. A process according to claim 5 wherein X represents a radical of the formula

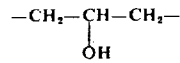

11. A process according to claim 5 wherein the compound is selected from those of the general formula

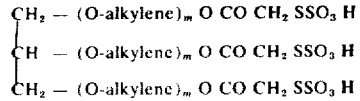

where $m$ has the same meaning as in claim 9 and alkali metal, ammonium and amine salts thereof.

12. A process according to claim 5 wherein the compound is selected from those of the general formula

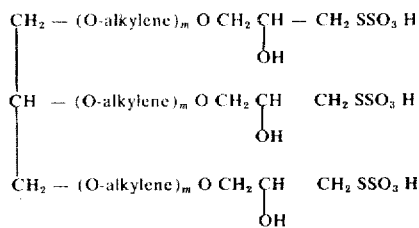

wherein $m$ has the same meaning as in claim 9 and alkali metal, ammonium and amine salts thereof.

13. A process according to any 1, wherein the amount of resin applied to the fibres is 0.1 to 10% by weight on the weight of fibre.

14. A process according to claim 1 wherein the resin is applied in the presence of thiourea or thioglycerol.

15. A process according to claim 1 wherein the resin is applied in aqueous solution.

16. A process according to claim 1 wherein said curing step is effected with an aqueous solution of an acid, a base, a Lewis acid, a substance containing thiol groups, an amine, thiourea, thioglycerol, thiocyanate or iodide ions.

17. A process according to claim 1 wherein the fibres are further treated with aqueous magnesium chloride and/or ammonium thioglycollate.

18. A process according to claim 1 wherein the fibres comprise keratinous fibres.

19. A process according to claim 2 wherein the polymeric compound is applied to the fibres in the presence of a wool dye.

20. A process according to claim 19 wherein the wool dye is an acid levelling, acid milling, 1:1 or 1:2 — premetallised or reactive dye.

21. A process according to claim 19 wherein the dye and polymeric compound are applied by exhaustion at the boil.

22. A process according to claim 19 which comprises applying to wool fibres by padding a composition comprising a polymeric compound as defined in claim 1, an acid levelling, acid milling, 1:1 or 1:2 — premetallised or reactive dye, an acid amide or thioamide, and a reducing agent for keratin, storing the impregnated fibres in the presence of moisture for 10 secs-72 hours and then washing the fibres.

23. A process according to claim 1 for pigment dyeing of synthetic fibres or filaments, in which the compound is applied together with a pigment and then cured.

24. A process according to claim 23 wherein the synthetic fibres or filaments are polyester fibres or filaments.

25. A process according to claim 1 wherein the fibrous or filamentary material is a textile fibre.

26. A process according to claim 1 wherein the fibrous or filamentary material is a textile fabric.

* * * * *